(12) United States Patent
Cox

(10) Patent No.: US 9,731,259 B2
(45) Date of Patent: Aug. 15, 2017

(54) FUNCTIONAL FLUID

(71) Applicant: Thos. Bentley & Son Limited, Leeds, West Yorkshire (GB)

(72) Inventor: Russell Cox, Leeds (GB)

(73) Assignee: THOS. BENTLEY & SON LIMITED, Leeds (GB)

( * ) Notice: Subject to any disclaimer, the term of this patent is extended or adjusted under 35 U.S.C. 154(b) by 0 days.

(21) Appl. No.: 14/784,468

(22) PCT Filed: Apr. 10, 2014

(86) PCT No.: PCT/GB2014/051119
§ 371 (c)(1),
(2) Date: Oct. 14, 2015

(87) PCT Pub. No.: WO2014/170641
PCT Pub. Date: Oct. 23, 2014

(65) Prior Publication Data
US 2016/0051953 A1   Feb. 25, 2016

(30) Foreign Application Priority Data

Apr. 15, 2013   (GB) .................................. 1306815.0

(51) Int. Cl.
| | |
|---|---|
| *B01F 17/00* | (2006.01) |
| *A61Q 5/02* | (2006.01) |
| *A61Q 5/12* | (2006.01) |
| *A61Q 9/02* | (2006.01) |
| *A61Q 17/04* | (2006.01) |
| *A61K 8/06* | (2006.01) |
| *A61Q 19/10* | (2006.01) |
| *A61Q 19/00* | (2006.01) |
| *A61K 8/92* | (2006.01) |
| *A61K 8/37* | (2006.01) |
| *C07C 69/58* | (2006.01) |
| *C07C 69/52* | (2006.01) |
| *C11D 3/20* | (2006.01) |
| *C11D 7/26* | (2006.01) |
| *C11D 17/00* | (2006.01) |

(52) U.S. Cl.
CPC ............ *B01F 17/0092* (2013.01); *A61K 8/06* (2013.01); *A61K 8/062* (2013.01); *A61K 8/375* (2013.01); *A61K 8/922* (2013.01); *A61Q 5/02* (2013.01); *A61Q 5/12* (2013.01); *A61Q 9/02* (2013.01); *A61Q 17/04* (2013.01); *A61Q 19/00* (2013.01); *A61Q 19/10* (2013.01); *C07C 69/52* (2013.01); *C07C 69/58* (2013.01); *C11D 3/2093* (2013.01); *C11D 7/266* (2013.01); *C11D 17/0017* (2013.01)

(58) Field of Classification Search
CPC .......... A61K 8/06; A61K 8/062; A61K 8/375; A61K 8/922; A61Q 17/04; A61Q 19/00; A61Q 19/10; A61Q 5/02; A61Q 5/12; A61Q 9/02; B01F 17/0092; C07C 69/52; C07C 69/58; C11D 17/0017; C11D 3/2093
See application file for complete search history.

(56) References Cited

U.S. PATENT DOCUMENTS

| | | |
|---|---|---|
| 2,154,977 A | 4/1939 | Reginald et al. |
| 4,456,627 A | 6/1984 | Van Heteren et al. |
| 5,147,644 A | 9/1992 | Oppenlaender et al. |
| 5,380,469 A | 1/1995 | Flider |
| 5,397,497 A | 3/1995 | Jakobson et al. |
| 5,424,469 A | 6/1995 | Jakobson et al. |
| 5,736,581 A | 4/1998 | Ansmann et al. |
| 5,840,943 A | 11/1998 | Ansmann et al. |
| 6,242,499 B1 | 6/2001 | Gruning et al. |
| 2002/0058781 A1 | 5/2002 | Lemke |

FOREIGN PATENT DOCUMENTS

| | | |
|---|---|---|
| CA | 2571906 A1 | 6/2008 |
| JP | 07145104 A | 6/1995 |
| SU | 802261 A1 | 2/1981 |
| WO | 8101286 | 5/1981 |
| WO | 2008103289 A1 | 8/2008 |

OTHER PUBLICATIONS

Search Report for Application No. GB1117394.5, dated Feb. 10, 2012, 7 pages.
International Search Report and Written Opinion for Application No. PCT/GB2014/051119, mailed Jul. 8, 2014, 10 pages.

*Primary Examiner* — Aradhana Sasan
(74) *Attorney, Agent, or Firm* — Hoffman Warnick LLC

(57) ABSTRACT

A functional fluid useful as an emulsion in a cleaning product or a personal care product is the esterification reaction product of a) a triglyceride or a fatty acid or a methyl ester of a fatty acid, and b) an alcohol which comprises b1) a polyglycerol having at least 3 glycerol units (preferably polyglycerol-4), and b2) glycerol and/or diglycerol. The functional fluid is effective as a stabilizer and as an emulsifier for o/w and w/o emulsions. When a triglyceride is used as a reactant, glycerol and fatty acids are generated in situ by an interesterification reaction. Preferred functional fluids provide the significant benefit that they may be mixed into an oil phase and in a water phase before such phases are mixed together, and that such processing may be carried out at ambient temperature.

15 Claims, No Drawings

FUNCTIONAL FLUID

CROSS-REFERENCE TO RELATED APPLICATIONS

This application is a US national stage of International Patent Application No. PCT/GB2014/051119, filed 10 Apr. 2014, which claims priority to Great Britain Patent Application No. 1306815.0, filed 15 Apr. 2013, each of which is incorporated herein as though fully set forth.

This invention relates to a functional fluid for use in promoting or maintaining a required form of composition, for example, an emulsion or solution, suitable as a cleaning product or a personal care product.

There is an ever-present need for functional fluids which are effective as emulsifiers and stabilisers and offer the skilled person new formulation possibilities or processing benefits.

In accordance with a first aspect of the present invention there is provided a functional fluid for use in the preparation of a cleaning product or a personal care product, wherein the functional fluid is the esterification reaction product of a) a triglyceride, or a fatty acid, or a methyl ester of a fatty acid, and b) a polyhydric alcohol which comprises b1) a polyglycerol having at least 3 glycerol units, and b2) glycerol and/or diglycerol.

The triglyceride may be an oil or fat. Preferably it is an oil (being a liquid at ambient temperature of 18° C.). It may be a hydrogenated derivative. Preferably, however, the triglyceride is a naturally-occurring oil, or fat, whose structure has not been chemically modified prior to the esterification reaction.

The triglyceride or the fatty acid or the methyl ester of a fatty acid may be of animal or, preferably, of plant origin.

Batches of triglycerides may vary in their average molecular weight and in their distribution of components but the values stated in this specification define typical situations.

The triglyceride, or the parent triglyceride of the fatty acid or methyl ester of a fatty acid, may be from a single triglyceride source, for example a single named oil or fat, or from a plurality of triglyceride sources, blended.

The fatty acid moieties of the triglyceride, or of the fatty acid or of the methyl ester of a fatty acid, each have an R—CO— moiety, where R represents a hydrocarbyl moiety. Preferably there are at least 6 carbon atoms in the R—CO— moiety, preferably at least 8 carbon atoms; preferably at least 10 carbon atoms; most preferably at least 12 carbon atoms. Preferably there are up to 36 carbon atoms in the R—CO— moiety, preferably up to 28 carbon atoms, preferably up to 24 carbon atoms, more preferably up to 20 carbon atoms.

Suitably fats or oils for use in the esterification reaction may be selected from one or more of the following: almond oil, babassu oil, borage oil, canola oil, cocoa butter, coconut oil, corn oil (maize oil), cottonseed oil, flaxseed oil, grape seed oil, hazelnut oil, illipe, oat oil, olive oil, palm oil, palm olein, palm kernel oil, peanut oil, rapeseed oil, safflower oil, sesame oil, shea nut, soybean oil, tucum oil, sunflower oil, walnut oil, apricot oil, sweet almond oil, avocado oil, baobab oil, blueberry seed oil, calendula oil, camellia oil, cherry kernel oil, cranberry seed oil, hemp oil, jojoba oil, kukur nut oil, macadamia nut oil, manketti oil, melon seed oil, moringe oil, peach kernel oil, pistachio oil, raspberry seed oil, rice bran oil, rosehip oil, soya oil, wheatgerm oil, yangu oil; and their hydrogenated derivatives. A blend of oils or fats may be employed.

Fatty acids or methyl esters of fatty acids, which may be used in the esterification reaction, may include fatty acids or methyl esters derived from any of the fats or oils described above.

Fatty acids which may be used in the esterification reaction, or which may be regarded as 'delivered' to the esterification reaction by a fat or oil, may be selected from one or more of the following: caproic acid, caprylic acid, capric acid, lauric acid, myristic acid, palmitic acid, palmitoleic acid, stearic acid, oleic acid, ricinoleic acid, vaccenic acid, linoleic acid, alpha-linolenic acid (ALA), gamma-linolenic acid (GLA), arachidic acid, gadoleic acid, arachidonic acid (AA), EPA (5,8,11,14,17-eicosapentaenoic acid), behenic acid, erucic acid, DHA (4,7,10,13,16,19-docosahexaenoic acid), and lignoceric acid; and methyl esters of such acids. A blend of fatty acids and/or fatty acid methyl esters may be employed.

Especially preferred acids include caproic acid, caprylic acid, capric acid, lauric acid, myristic acid, palmitic acid, stearic acid, linoleic acid, alpha-linolenic acid (ALA)—and gamma-linoleic acid (GLA). Especially preferred methyl esters may be methyl esters of such fatty acids. Oils or fats which yield such fatty acids are preferred oils or fats. Especially preferred oils are flax seed (flax) oil (which can yield alpha-linolenic acid, ALA), borage seed (borage) oil (which can yield gamma-linolenic acid, GLA) and palm kernel oil (which can yield palmitic acid).

The fatty acid moieties, whether as free acids or methyl esters thereof or as components of a triglyceride, may be saturated or unsaturated. If unsaturated they may suitably have from 1 to 6 double bonds, preferably 1 to 3 double bonds. The fatty acids or methyl esters or parent oils or fats may have been hydrogenated.

In one embodiment the fatty acid moieties, whether free acids or methyl esters thereof or as a component of a triglyceride, are saturated fatty acid moieties having an average molecular weight of less than 282 g/mol, preferably less then 260 g/mol, preferably less than 240 g/mol.

In one embodiment the fatty acid moieties, whether free acids or methyl esters thereof or as a component of a triglyceride, are unsaturated fatty acid moieties having an average molecular weight of less than 320 g/mol, preferably less than 300 g/mol.

The reactant a) may be a triglyceride or a fatty acid or a fatty acid methyl ester or any combination thereof.

Batches of polyglycerols may vary in their average molecular weight and in their distribution of components but the values stated in this specification define typical situations or typical average values.

Preferably the polyglycerol component b1) comprises polyglycerol-4.

Polyglycerol-4 is a commercially available product sold under that name. As with any such polyglycerol materials, polyglycerol-4 is a distribution of a polyglycerol compounds in which the compound tetraglycerol may be regarded as the most significant compound. The definitions given above apply. Thus, for example, the compound tetraglycerol may be the major compound present by weight; and/or the average molecular weight of the polyglycerol may be centred on polyglycerol-4.

Preferably the polyglycerol component b1) comprises at least 50% wt of polyglycerol compounds composed of 3 to 6 glycerol units, preferably at least 60% wt, preferably at least 70% wt, most preferably at least 85% wt.

Preferably the polyglycerol component b1) comprises at least 20% wt of the compound tetraglycerol, preferably at least 25% wt, preferably at least 30% wt, preferably at least 35% wt, most preferably at least 40% wt.

In some embodiments the polyglycerol component b1) comprises at least 45% wt of the compound tetraglycerol, preferably at least 50% wt, most preferably at least 55% wt.

Preferably the compound tetraglycerol is present in the polyglycerol component b1) in substantially the same amount or in a higher amount by weight than the compound triglycerol.

Preferably the compound tetraglycerol is present in the polyglycerol component b1) in a higher amount by weight than the compound pentaglycerol.

Preferably the compound tetraglycerol is the single compound present in the largest proportion by weight in the polyglycerol component b1).

In commercial sources of polyglycerol-4, which may be used in the present invention as a preferred component b1), the proportions by weight of compounds is typically as follows:
- triglycerol, 25-50% wt
- tetraglycerol, 25-50% wt
- higher polyglycerols, 15-40% wt
- other compounds, not more than 20% wt, typically less than 12% wt.

Higher polyglycerols herein means polyglycerol compounds formed of 5 or more glycerol units.

The other compounds may include water and diglycerol. Small amounts of glycerol may sometimes be present.

When glycerol and/or diglycerol is/are present in the polyglycerol source they may supply some or all of the component b2). However the amount of glycerol and diglycerol in a polyglycerol source is generally low. Therefore, in such embodiments, it is generally required to supply glycerol and/or diglycerol to reach the desired amount. This may be done by simple addition of glycerol and/or diglycerol. When a triglyceride is used it may occur by the liberation of glycerol in the esterification reaction.

Preferably the average molecular weight of the polyglycerols in component b1), having at least 3 glycerol units, is in the range 220-500 g/mol, preferably 230-450 g/mol, preferably 240-420 g/mol, preferably 250-400 g/mol, preferably, preferably 260-370 g/mol, 280-350 g/mol, most preferably 300-330 g/mol.

Preferably glycerol constitutes at least 60% wt of the component b2), preferably at least 70% wt, preferably at least 80% wt.

Preferably the ratio by weight of the component b2) to component b1) is one part b2) to at least 4 parts b1), preferably one part b2) to at least 6 parts b1), and most preferably at least one part b2) to at least 8 parts b1).

Preferably the ratio by weight of the component b2) to component b1) is one part b2) to up to 24 parts b1), preferably one part b2) to up to 20 parts b1), and most preferably one part b2) to up to 16 parts b1).

Preferably the components b1) and b2) make up at least 50% wt of the functional fluid, preferably at least 60% wt, preferably at least 70% wt, preferably at least 80% wt, preferably at least 90% wt.

When a triglyceride is employed in this invention the reaction may be regarded as an interesterification reaction. As noted above glycerol liberated in the reaction may provide some or all of component b2). Preferably it provides all of the glycerol comprised by component b2). Glycerol could be removed or added. Preferably, no glycerol is removed. Preferably, when a triglyceride is used, no glycerol is added.

When a fatty acid or fatty acid methyl ester is used for the esterification reaction, component b2) is added to the reaction mixture, suitably in such an amount as to satisfy at least one of the b1):b2) definitions given above.

When a triglyceride is used, preferably the molar ratio of the polyglycerol to the triglyceride in the reaction mixture, based on average molecular weights, is 0.5-5 to 1, preferably 1-4 to 1, preferably 1.5-3 to 1, most preferably 2-2.5 to 1. Average molecular weight may be determined by normal measures. In the case of the triglyceride this may be from GC results. In the case of polyglycerol the raw material specifications may be used.

When a fatty acid or derivative is used, the molar ratio of the polyglycerol to the fatty acid in the reaction mixture, based on average molecular weights, is 0.2-3 to 1, preferably 0.3-2 to 1, preferably 0.5-1.5 to 1, most preferably 0.7-1.3 to 1.

"Esterification" herein includes transesterification or interesterification.

Standard esterification conditions may be used. Suitably reactions which employ triglycerides are carried out under alkaline conditions (e.g. by addition of sodium hydroxide or potassium hydroxide) and at elevated temperature, for example at least 150° C., preferably 200-250° C. Suitably reactions which employ fatty acids added to the reaction mixture are carried out under acidic conditions (e.g. by addition of sulphonic acid or orthophosphoric acid) and at elevated temperature, for example at least 150° C., preferably 200-250° C.

Preferably the functional fluid is a liquid at ambient temperature of 18° C.

Preferably the process is a one-pot process, even when it employs a triglyceride.

Preferably the functional fluid is the product of the esterification reaction, without work up (other than neutralisation of any catalyst present).

Preferably the reaction composition, which indicates the functional fluid without work up, is a liquid at ambient temperature of 18° C.

A liquid herein may include a thin free-flowing liquid or a viscous liquid or a pasty material; or any substantially incompressible material which can be made to flow under moderate force; for example under gravity or on being squeezed from a bottle or tube.

Preferably the functional fluid is soluble in a triglyceride to a concentration of at least 0.5% wt, preferably at least 1% wt, preferably at least 2% wt, preferably at least 4% wt, preferably at least 6% wt. and most preferably at least 8% wt.

Preferably the functional fluid is soluble in water to a concentration of at least 0.5% wt, preferably at least 1% wt, preferably at least 2% wt, preferably at least 4% wt, preferably at least 6% wt. and most preferably at least 8% wt.

Preferably the functional fluid is soluble both in a triglyceride in an amount as stated above, and in water in an amount as stated above.

The solubility levels stated above refer to solubility at atmospheric pressure and at ambient temperature of 18° C.

Preferably the functional fluid comprises a plurality of esters, formed from the range of triglycerides present in oil or fat (or from the range of fatty or methyl esters obtained from such triglycerides), and the range of polyglycerol compounds present in an as-supplied "polyglycerol" source. The functional fluid may comprise many esters, for example over 20 ester compounds, or over 50 ester, or over 100 ester.

In a second aspect of the invention there is provided a cleaning product or a personal care product, being a formulation of an oil phase and a water phase in which the functional fluid as defined in the first aspect is an emulsifier or stabiliser or dispersant or suspension aid. Preferably it is the only emulsifier or stabiliser or dispersant or suspension aid present. An emulsion may be an o/w or w/o emulsion (although the formation of o/w/o or w/o/w emulsions is not excluded from the scope of this invention).

In some embodiments the formulation comprises a binder or viscosity modifier. A suitable binder or viscosity modifier is a hydrocolloid.

The binder or viscosity modifier may be of animal or, preferably, of plant origin.

A preferred binder or viscosity modifier is selected from agar, an alginate, gum arabic, guar gum, locust bean gum, pectin, tragacanth and xanthan gum. Xanthan gum is particularly preferred.

Preferably a binder or viscosity modifier may be present in the emulsion in an amount of at least 0.01% wt, preferably at least 0.04% wt, preferably at least 0.08% wt.

Preferably a binder or viscosity modifier may be present in the emulsion in an amount up to 3% wt, preferably up to 2% wt, preferably up to 1% wt, preferably up to 0.5% wt.

Preferably the binder or viscosity modifier, when present, is added to the water phase, before it is brought together with the oil phase, to form the emulsion.

In a third aspect of the invention there is provided a method of making a formulation of the second aspect, wherein the functional fluid is mixed into the oil phase, or into the water phase, or into both, before the oil phase and the water phase are mixed.

Overall, the formulation preferably contains at least 0.5% wt, preferably at least 1% wt, preferably at least 1.5% wt, of the functional fluid.

Overall, the formulation preferably contains up to 10% wt, preferably up to 8% wt, preferably up to 6% wt, preferably up to 6% wt, of the functional fluid.

Preferably the functional fluid is added to the oil phase, or into the water phase, or into both, in the form of the reaction product described above.

When the functional fluid is mixed into the oil phase, before the oil phase and the water phase are mixed together, it is preferably introduced in an amount of at least 0.5% wt, preferably at least 1% wt, preferably in an at least 1.5% wt of the oil phase.

When the functional fluid is mixed into the oil phase, before the oil phase and the water phase are mixed together, it is preferably introduced in an amount up to 10% wt, preferably up to 8% wt, preferably up to 6% wt, more preferably up to 5% wt, or the oil phase.

When the functional fluid is mixed into the water phase, before the oil phase and the water phase are mixed together, it is preferably introduced in an amount of at least 0.5% wt, preferably at least 1% wt, preferably at least 1.5% wt, of the water phase.

When the functional fluid is mixed into the water phase, before the oil and the water phase are mixed together, it is preferably introduced in an amount up to 10% wt, preferably up to 8% wt, preferably up to 6% wt, preferably up to 5% wt of the water phase.

In one embodiment the functional fluid is mixed into the oil phase, and not to the water phase, before the oil phase and the water phase are mixed together.

In another preferred embodiment a functional fluid (preferably the same functional fluid) is mixed into both the oil phase and the water phase, before the oil phase and the water phase are mixed together.

The functional fluid is suitably mixed into the oil phase at a moderate temperature, suitably not exceeding 50° C., preferably not exceeding 30° C.

Preferably the functional fluid is mixed into the oil phase at a temperature in the range 15-30° C., for example ambient temperature.

Preferably the functional fluid is suitably mixed into the water phase at a moderate temperature, suitably not exceeding 50° C., preferably not exceeding 30° C.

The functional fluid is mixed into the water phase at a temperature in the range 15-30° C., for example ambient temperature.

Suitably the oil phase and the water phase are mixed together at a moderate temperature, suitably not exceeding 50° C., preferably not exceeding 30° C. Preferably they are mixed together at a temperature in the range 15-30° C., for example ambient temperature.

For any of the mixing steps described above (including mixing of the functional fluid into either phase, and mixing of the phases together), active and/or high-shear mixing could be employed. Preferably, however, low-shear mixing is employed, for example simple stirring or tumbling.

Suitably the formulation of the second aspect, or the formulation produced by the method of the third aspect, is an emulsion. The functional fluid may be the only emulsifier present, or may be a co-emulsifier.

Alternatively the formulation of the second aspect, or the formulation produced by the method of the third aspect, may be a suspension or dispersion of an oil phase and a water phase; wherein the functional fluid, as defined in the first aspect, is present as a suspension aid or dispersant or stabiliser, which acts to keep the formulation in a desires physical state.

Such an aqueous solution preferably contains at least 0.5% wt, at least 1% wt, preferably at least 1.5% wt, preferably at least 2% wt, more preferably at least 3% wt, of the functional fluid.

Such an aqueous solution preferably contains up to 10% wt, preferably up to 8% wt, preferably up to 6% wt, preferably up to 5% wt, of the functional fluid.

An essential oil, for example a fragrance oil, may be present.

An essential oil may be present in an amount of from 0.05% wt, preferably from 0.1% wt, preferably from 0.15% wt, preferably from 0.2% wt. The upper limit of the dissolved oil is its solubility limit in the aqueous phase at atmospheric pressure and 20° C. but is typically not greater than 0.5% wt, and typically not greater than 0.3% wt.

The aqueous solution may contain a cleaning agent or surfactant, for example sodium lauryl ether sulphate (SLES) and/or a betaine surfactant.

A formulation of the second aspect or a formulation produced by the method of the third aspect is suitably a personal cleaning product, for example a shower gel, shampoo, hair conditioner, shaving or skincare product, including a body wash or sunscreen product; a household cleaning product, for example a hard surface cleaner (e.g. for tiles, ovens, floors, kitchen work surfaces, windows); a dishwashing or laundering product; or a vehicle cleaning product.

The invention will now be further described by way of illustration with reference to the following example:

EXAMPLE 1—PALM KERNEL OIL+POLYGLYCEROL-4

| | |
|---|---|
| Palm kernel oil (average Mw = 722) = | 722 g |
| Polyglycerol-4 (average Mw = 250) = | 550 g |
| NaOH = | 0.2 g |

Procedure:

Charge oil to reaction vessel, charge in polyglycerol-4, warm to melt reagents, when temperature reaches 50° C. charge in NaOH. Evacuate headspace with vacuum pump, break vacuum with nitrogen, repeat purge and refresh $N_2$ blanket on reaction. Heat to 220 to 240° C. When at this temperature apply vacuum and monitor reaction visually—reaction mixture becomes transparent after 1 hour at 220° C.

Check TLC of reaction (toluene 80%, chloroform 15%. methanol 5%). Visualise with potassium permanganate stain showing complete reaction of triglyceride. Cool to room temperature. At 90° C. add phosphoric acid (0.2 g) to neutralise catalyst. Carry out cooling under $N_2$ atmosphere.

Product: recovery=1200 g pale amber oil: viscous at ambient temperature

The resulting polyglycerol ester product was able to produce a stable emulsion by the mixing together of an oil phase and an oil phase, as described in examples which follow.

EXAMPLE 2—FLAX OIL+POLYGLYCEROL-4

| | |
|---|---|
| Flax oil (average Mw = 872) = | 872 g |
| Polyglycerol-4 (average Mw = 250) = | 550 g |
| NaOH = | 0.2 g |

Procedure:

Reaction as described for Example 1. Reaction became transparent after 45 minutes. TLC confirmed reaction of all triglyceride.

Product: recovery=1375 g pale amber viscous oil

The resulting polyglycerol ester product was able to produce a stable emulsion by the mixing together of an oil phase and an oil phase, for example following the procedure on Example 5 below.

EXAMPLE 3—BORAGE OIL+POLYGLYCEROL-4

| | |
|---|---|
| Borage oil (average Mw = 879) = | 879 g |
| Polyglycerol-4 (average Mw = 250) = | 550 g |
| NaOH = | 0.2 g |

Reaction carried out as per Example 1. Reaction went transparent after 50 minutes at 200° C. TLC indicated all triglyceride consumed.

Product: recovery=1385 g pale green viscous oil

The resulting polyglycerol ester product was able to produce a stable emulsion by the mixing together of an oil phase and an oil phase, for example following the procedure on Example 5 below.

EXAMPLE 4—OLEIC ACID+POLYGLYCEROL-4 ESTER

| | |
|---|---|
| Oleic acid (average Mw = 282) = | 275 g |
| Polyglycerol-4 (average Mw = 250) = | 182 g |
| Glycerol = | 30.7 g |
| Orthophosphoric acid = | 1 drop |

Procedure: charge reagents to reaction vessel, evacuate headspace with vacuum, break with $N_2$—repeat, heat reaction to 220° C. under $N_2$ blanket. Monitor reaction for 3 hours measuring free fatty acid content. Collect water from reaction distillation after 3 hours. FFA=0.2%. Reaction was now complete.

Product: recovery=468 g pale viscous oil

The resulting polyglycerol ester product was able to produce a stable emulsion by the mixing together of an oil phase and an oil phase, for example following the procedure on Example 5 below.

EXAMPLE 5—EMULSIFIER STUDIES WITH POLYGLYCEROL ESTERS

Assessments of the polyglycerol esters of Example 1 in forming emulsions under ambient conditions were carried out.

Base Formulation:

| | | |
|---|---|---|
| Water = | 78.9% wt (to 100%) | ) in water phase |
| Polyglycerol-4 ester = | 1.5% wt (ex. Ex. 4) | ) |
| Xanthan gum = | 0.1% wt (binder) | ) |
| Oil (olive) = | 15% wt | ) in oil phase |
| Polyglycerol-4 ester = | 1.5% wt (ex. Ex. 1) | ) |

The two phases were each prepared at ambient temperature (18° C.), using a magnetic stirrer. One phase was added to the other and stirred at ambient temperature (18° C.) for 5 minutes.

The resulting emulsion was a low viscosity odourless emulsion.

The stability of the emulsion was determined by weekly monitoring of undisturbed samples stored under different controlled conditions—one in an oven at 40° C., one at ambient temperature in ambient light, and one at ambient temperature in the dark; before an overall assessment was made. The testing was concluded after 12 weeks. The test is an accelerated test designed to equate to 12 months if the formulation is held at ambient temperature. In this manner the emulsion was determined to have excellent stability.

EXAMPLE 6—EMULSIFIER STUDIES WITH POLYGLYCEROL ESTERS

An emulsion was prepared with the following components:

| | | |
|---|---|---|
| Water | to 100% wt | ) |
| Microcare PE | 0.7% wt | ) water phase |
| Xanthan gum | 0.2% wt | ) |
| Polyglycerol-4 ester of Ex. 1 | 2.5% wt | ) |

-continued

| | | | |
|---|---|---|---|
| Sunflower oil | 40% wt | ) | oil phase |
| Polyglycerol-4 ester of Ex. 1 | 4% wt | ) | |

Microcare PE is a preservative based on chloromethyl-isothiazolinone and methylisothiazolinone The two phases were each prepared at ambient temperature (18° C.), using a magnetic stirrer. One phase was added to the other and stirred at ambient temperature (18° C.) for 5 minutes.

The product was stable over an extended period. In particular, there was no separation of the oils. Without the oil—polyglycerol ester no emulsion would form, or under certain mixing conditions there could be an emulsion formed, of short duration.

EXAMPLE 7—STABILISATION WITH POLYGLYCEROL ESTERS

A foaming lotion was prepared with the following components:

| | | | |
|---|---|---|---|
| Water | to 100% wt | ) | |
| Carbopol ultrez 20 | 0.75% wt | ) | water phase |
| Euxyl 9010PE | 0.7% wt | ) | |
| Sunflower oil | 5% wt | ) | |
| Palm kernel oil | 5% wt | ) | oil phase |
| Polyglycerol-4 ester of Ex. 1 | 0.75% wt | ) | |
| Potassium citrate | 1% wt | ) | electrolyte phase |
| Palm kernel liquid soap | 4% wt | ) | |

Carbopol ultrez 20 is a viscosity modifier based on hydrophobically modified cross-linked polyacrylate Euxyl 901 OPE is a preservative based on phenoxyethanol The components of the water phase were mixed until the Carbopol is fully wetted, using an overhead stirrer. The components of the oil phase were mixed using an overhead stirrer, and the oil phase was added to the water phase, with stirring.

The potassium citrate was added, and the mixture became viscous. The remaining ingredients were added in the order stated and the composition stirred until homogeneous (approximately 15 minutes). The entire process was approximately carried out at ambient temperature (18° C.). The lotion has excellent foaming properties.

The invention claimed is:

1. A functional fluid comprising: an esterification reaction product of a) a triglyceride and b) a polyhydric alcohol which comprises b1) a polyglycerol having at least 3 glycerol units, and b2) at least one of glycerol or diglycerol, wherein the polyglycerol component b1) comprises at least 25 wt % of the compound tetraglycerol.

2. The functional fluid as claimed in claim 1, wherein the polyglycerol component b1) comprises at least 50% wt of polyglycerol compounds composed of 3 to 6 glycerol units.

3. The functional fluid of claim 1, wherein the proportions by weight of compounds is as follows:
triglycerol, 25-50% wt
tetraglycerol, 25-50% wt
higher polyglycerols, 15-40% wt
other compounds, not more than 20% wt.

4. The functional fluid of claim 1, wherein the average molecular weight of the polyglycerols in component b1), having at least 3 glycerol units, is in the range 220-500 g/mol.

5. The functional fluid of claim 1, wherein the polyhydric alcohol component b1) comprises the product polyglycerol-4.

6. The functional fluid of claim 1, wherein diglycerol constitutes at least 60% wt of the component b2).

7. The functional fluid of claim 1, wherein a glycerol liberated in the esterification reaction provides all of the glycerol comprised by component b2).

8. A cleaning product or a personal care product comprising a formulation of oil and water; and a quantity of the functional fluid of claim 1 as an emulsifier or stabiliser or dispersant or suspension aid.

9. A cleaning product or a personal care product as claimed in claim 8, containing at least 0.5% wt, of the functional fluid.

10. A cleaning product or a personal care product of claim 8, which is a personal cleaning product selected from a group consisting of: a shower gel, shampoo, hair conditioner, shaving product, or skincare product, a body wash, a sunscreen; or a hard surface cleaner; or a dishwashing or laundering product; or a vehicle cleaning product.

11. A method of making a product according to claim 8, the method comprising mixing the functional fluid into the oil phase in an amount of at least 0.5% wt, or into the water phase in an amount of at least 0.5% wt, or into both the water phase and the oil phase in an amount of at least 0.5% wt in each phase, before such phases are mixed together.

12. A method as claimed in claim 11 wherein the same functional fluid is mixed into the oil phase, and into the water phase, before such phases are mixed together.

13. A method as claimed in claim 11, in which each step of the method takes place at a temperature not exceeding 50° C.

14. A method as claimed in claim 13, in which each step of mixing the functional fluid into the oil phase and/or the water phase and the mixing together of the oil and water phases, takes places at a temperature in the range 15-30° C.

15. A functional fluid comprising: an esterification reaction product of a) a fatty acid or a methyl ester of a fatty acid, and b) a polyhydric alcohol which comprises b1) a polyglycerol having at least 3 glycerol units, and b2) glycerol,
wherein the polyglycerol component b1) comprises at least 25% wt of the compound tetraglycerol.

* * * * *

UNITED STATES PATENT AND TRADEMARK OFFICE
CERTIFICATE OF CORRECTION

PATENT NO. : 9,731,259 B2  
APPLICATION NO. : 14/784468  
DATED : August 15, 2017  
INVENTOR(S) : Russell Cox Page 1 of 1

It is certified that error appears in the above-identified patent and that said Letters Patent is hereby corrected as shown below:

In the Specification

Please insert at Column 9, Line 33 --Cocoamidopropyl betaine 16 %wt )--.

Signed and Sealed this  
Twenty-sixth Day of September, 2017

Joseph Matal  
*Performing the Functions and Duties of the*  
*Under Secretary of Commerce for Intellectual Property and*  
*Director of the United States Patent and Trademark Office*